United States Patent [19]

Gubitosa et al.

[11] Patent Number: 5,543,379
[45] Date of Patent: Aug. 6, 1996

[54] HYDROGENATION CATALYST, AND A METHOD FOR ITS PREPARATION AND USE, IN PARTICULAR FOR HYDROGENATION AND/OR HYDROGENOLYSIS OF CARBOHYDRATES AND POLYHYDRIC ALCOHOLS

[75] Inventors: Giuseppe Gubitosa, Novara; Bruno Casale, Cameri, both of Italy

[73] Assignee: Montecatini Technologie S.r.l., Italy

[21] Appl. No.: 221,810

[22] Filed: Apr. 1, 1994

Related U.S. Application Data

[62] Division of Ser. No. 11,189, Jan. 29, 1993, Pat. No. 5,326,912.

[30] Foreign Application Priority Data

Jan. 31, 1992 [IT] Italy ................................. TO92A0080

[51] Int. Cl.$^6$ ................................. B01J 23/46; B01J 23/72
[52] U.S. Cl. ......................... 502/184; 502/185; 502/331; 502/339; 502/345
[58] Field of Search ......................... 502/184, 185, 502/330, 331

[56] References Cited

U.S. PATENT DOCUMENTS

| | | | |
|---|---|---|---|
| 3,901,827 | 8/1975 | Sinfelt et al. ........................... | 502/331 |
| 4,111,842 | 9/1978 | van Montfoort et al. ............... | 502/184 |
| 4,743,577 | 5/1988 | Schroeder et al. ...................... | 502/331 |
| 4,787,969 | 11/1988 | Baird, Jr. ................................ | 208/139 |
| 5,149,680 | 9/1992 | Kitson et al. ........................... | 502/184 |
| 5,326,912 | 7/1994 | Gubitosa et al. ....................... | 568/861 |

*Primary Examiner*—Anthony McFarlane
*Attorney, Agent, or Firm*—Bryan Cave LLP

[57] ABSTRACT

A metallic catalyst composition on an inert support, suitable in particular for hydrogenolysis reactions of higher polyhydric alcohols, characterized in that it comprises the following relative to 100 parts of the catalyst:

a) 0.5 to 5 weight % ruthenium;
b) 1 to 10 weight % of a metal selected from the group consisting of palladium, platinum and rhodium; and
c) 0.5 to 2.5 weight % copper, in which the copper content is lower than the content of the metal b).

The catalyst is used in particular for producing lower polyhydric alcohols such as ethanediol, propylene glycol, butanediol and glycerol, by means of hydrogenolysis reaction of higher polyhydric alcohols.

4 Claims, No Drawings

HYDROGENATION CATALYST, AND A METHOD FOR ITS PREPARATION AND USE, IN PARTICULAR FOR HYDROGENATION AND/OR HYDROGENOLYSIS OF CARBOHYDRATES AND POLYHYDRIC ALCOHOLS

This is a divisional of U.S. application Ser. No. 08/011,189, filed Jan. 29, 1993, U.S. Pat. No. 5,326,912.

The present invention relates to methods for hydrogenation of carbohydrates and hydrogenolysis of higher polyhydric alcohols, and to a new hydrogenation catalyst which is useful in particular for producing lower polyhydric alcohols from renewable materials, such as in particular carbohydrates and higher polyhydric alcohols.

In the present description, the term "higher polyhydric alcohols" means products such as sorbitol, mannitol and xylitol derived from catalytic hydrogenation of carbohydrates (and in particular of glucose, fructose and their mixtures).

The term "lower polyhydric alcohols" means polyalcohols having a maximum of 6 carbon atoms and a maximum of 3 hydroxyl groups, in particular ethanediol, propylene glycol, butanediol and glycerol.

The invention also relates to a method for preparing the new catalyst.

U.S. Pat. No. 2,868,847 describes a method for catalytic hydrogenation of mono- and disaccharides for producing polyhydroxyl alcohols, in particular sorbitol, and proposes replacing the known platinum and palladium-based catalysts used for this method, by a ruthenium catalyst or by a metallic catalyst based on ruthenium and platinum or palladium.

U.S. Pat. No. 4,476,331 describes a method for producing lower polyhydric alcohols comprising a first stage of hydrogenation of carbohydrates with production of higher polyhydric alcohols and a second stage in which the higher polyhydric alcohols are subjected to hydrogenolysis in the presence of a ruthenium-based catalyst which is pre-sulphurised or is sulphurised in use by addition of sulphurised compounds to the reactive medium. Sulphurisation of the ruthenium-based catalyst is necessary in order to limit the hydrogenolysis reaction which would otherwise lead to the formation of highly hydrogenated compounds (hydrocarbons, and in particular methane).

The main object of the present invention is to provide a method for hydrogenolysis of higher polyhydric alcohols which has a high selectivity towards the production of lower polyhydric alcohols, thus keeping to a minimum the formation of gaseous hydrocarbons which constitute an undesirable product.

For this purpose an object of the present invention is a new metallic catalyst on an inert support, characterised in that it comprises the following relative to the (anhydrous) weight of the catalyst:

a) 0.5 to 5 weight % ruthenium;

b) 1 to 10 weight % of a metal selected from the group consisting of palladium, platinum and rhodium; and c) 0.5 to 2.5 weight % copper, and in which the copper content is lower than the content of the metal b).

In particular use of palladium with a weight ratio of between 2 and 4 Pd/Cu is preferred in the catalyst.

A second object of the invention is a method for producing lower polyhydric alcohols and their mixtures by means of hydrogenolysis under pressure of higher polyhydric alcohols, in the presence of a metal catalyst on activated carbon consisting of the catalyst previously described.

The catalyst support preferably comprises powdered or granulated activated carbon. For continuous fixed bed hydrogenation and hydrogenolysis methods, a granulated activated carbon is preferably used, which has:

a specific surface area of 600 to 1000 $m^2/g$, preferably from 800 to 1000 $m^2/g$ (B.E.T. method);

a total pore volume of 0.5 to 1.2 $cm^3/g$ and preferably 0.6 to 0.7 $cm^3/gr$ (combined nitrogen-mercury method);

an apparent specific weight (bulk density) of 0.3 to 0.8 $gr/cm^3$ and preferably 0.45 to 0.55 $g/cm^3$;

an actual specific weight of 1.9 to 2.3 $g/cm^3$;

a total volume of micropores having a radius smaller than 75 A of 0.4 to 0.55 $cm^3/g$; and an ash content of 2 to 5 weight %

By granulated activated carbon is meant a carbon which has a minimum granule size of at least 0.5 mm and a particle size of between 5.7 and 0.5 mm (3–32 mesh; Tiller series). The optimum particle size is selected on the basis of the process parameters, according to known criteria.

Granulated activated carbon of the above-described type is available commercially from amongst the activated carbons produced by ACQUE NYMCO under references GH12132 and CA12132.

In the hydrogenolysis reaction of higher polyhydric alcohols, the catalyst preferably has:

a) 1 to 3 weight % ruthenium;

b) 2 to 6 weight % of the metal selected from amongst palladium, platinum and rhodium, and preferably palladium; and c) 0.5 to 2% weight copper.

The weight ratio between copper and the metal from group b) is preferably between 0.2 and 0.5.

The catalyst according to the invention is prepared by means of a method which comprises the following operations.

An aqueous solution is prepared which contains a compound of ruthenium and a second metal selected from amongst platinum, palladium and rhodium, with a concentration of the metals such that after the support has been impregnated, a concentration within the limits previously indicated of metal in the catalyst is obtained. The precursor used for the active elements is a ruthenium compound soluble in water, and preferably ruthenium trichloride, and a soluble compound of palladium, platinum or rhodium and preferably their chlorinated compounds such as $H_2PdCl_4$ and $Na_2PdCl_4$.

The aqueous solution containing the metals is then put into contact with an aqueous solution of the activated carbon, followed by adjustment of the pH by addition of an alkaline agent until a value of 4.5 to 8 is obtained; in the preferred embodiment the activated carbon is in the form previously described; when the aqueous solution of catalytic compounds has been put into contact with the suspension of the support, the pH of the suspension thus obtained is preferably allowed to stabilise at a value of approximately 1, and an aqueous solution of an alkaline compound is then added in a quantity such that the pH of the resulting suspension is between 4.5 and 5; after approximately an hour the pH is regulated by means of further addition of the alkaline agent to a value no higher than 8 and preferably to between 6 and 8.

The suspension is then heated to a temperature of between 70° and 100° C., and is preferably maintained at this temperature for a length of time which is generally between 30 minutes and 2 hours, and is sufficient to give rise to depositing of compounds of the metals on the activated carbon, which is then separated from the suspension; during this impregnation process the two metals are deposited in the support substantially in the form of highly dispersed oxides in close contact with one another, in concentrations of 0.5 to 5 weight % ruthenium and 0.1 to 10 weight % palladium, platinum or rhodium.

The separated solid thus obtained is then suspended in an alkaline solution, and the suspension thus obtained is processed with gaseous hydrogen at a temperature of between 60° and 100° C. for 1–4 hours and preferably for 3 hours; during this hydrogenation process the oxides, and in particular palladium oxide, are reduced to the metallic state.

An aqueous solution of copper is then added to the suspension at a temperature preferably lower than 50° C. An aqueous solution of copper formate is preferably used, in which the copper concentration is such that a concentration of 0.5 to 2.5 weight % copper is obtained on the support. The copper is easily reduced on the palladium and is deposited in the form of a metal in close contact with the two metals previously deposited on the activated carbon.

The alkaline agent used for adjustment of the pH may be a hydroxide, a carbonate or a bicarbonate of the alkaline elements, and preferably sodium carbonate.

The method for hydrogenolysis of higher polyhydric alcohols according to the invention is preferably carried out continuously on a fixed bed reactor. The reaction temperature is generally between 200° and 300° C. and preferably 220°–270° C., the spatial velocity of the fluid is between 0.3 and $4h^{-1}$ and preferably between 0.6 and 2.50 $h^{-1}$, and the reaction pressure is between 5 and 20 MPa and preferably between 7.5 and 15 MPa. The continuous reactor is preferably supplied with a reaction promoter selected from amongst alkaline and alkaline-earth hydroxides, and preferably sodium hydroxide or calcium hydroxide, or basic reaction salts; the molar ratio between higher polyhydric alcohols and the promoter supplied is between 2 and 30.

According to the hydrogenolysis method, the supply comprises a higher polyhydric alcohol or mixture of polyhydric alcohols, supplied to the hydrogenation reactor preferably in an aqueous solution having a concentration of 20 to 40 weight %.

The higher polyhydric alcohol or mixture of higher polyhydric alcohols is advantageously obtained in a first stage of hydrogenation of carbohydrates carried out with a low basic pH, preferably of between 7.5 and 8, at a reaction temperature of between 120° and 150° C. This first stage is also preferably carried out in an aqueous solution, in the presence of a basic promoter such as those previously described, in a quantity sufficient to maintain the pH in the aforementioned field. The reaction is preferably carried out in a fixed bed using a catalyst comprising 0.5 to 5 weight % ruthenium supported on granulated activated carbon having the above-described characteristics. The preparation of this catalyst is similar to that described for the catalyst comprising ruthenium, palladium and copper, the only difference being that the palladium and copper compounds are not used.

In this first stage the carbohydrate may comprise monosaccharides or disaccharides. The preferred supply however comprises an aqueous solution of glucose, which is converted with virtually maximum theoretical yield into sorbitol. Sorbitol constitutes the preferred supply substrate for the hydrogenolysis process which, owing to use of the catalyst according to the invention, enables ethanediol, 1.2-propylene glycol, butanediol, and smaller amounts of glycerol, lactic acid and monovalent alcohols, as well as products such as erythritol and pentanediols to be obtained with a high level of selectiveness.

The catalyst thus obtained has the characteristics of porosity, specific surface area and specific weight particular to the original activated carbon.

In this method the catalyst according to the invention enables the formation of undesirable gaseous hydrocarbons to be reduced without needing to use sulphurated compounds either in the catalyst or in the reactive medium.

EXAMPLE 1

Preparation of the catalyst.

For preparation of the catalyst according to the present invention, an activated carbon of vegetable origin and preferably derived from coconut (palm) having the following features is used:

specific surface area: 800 $m^2/g$ (B.E.T.); actual specific weight: 2.1 $g/cm^3$; total pore volume: 0.64 $cm^3/g$; volume of micropores (R>75 A): 0.5 $cm^3/g$; apparent specific weight (bulk density) 0.48 $g/cm^3$;

ash content: 3 weight %;

particle size: 10–18 mesh: (Tiller series 2÷1 mm): 20–30 weight % 18–35 mesh: (Tiller series 1÷0.5 mm): 80–70 weight %.

A quantity of 300 g granulated activated carbon of this type having 6% humidity is suspended in 2 liters of distilled water, washed preliminarily then filtered and suspended in a liter of distilled water, and continues to be subjected to mechanical agitation. After approximately 30 minutes the pH of the suspension is 10.

1 liter of solution of $RuCl_3$ and $Na_2PdCl_4$ containing 6 g Ru and 15 g Pd is added slowly and continuously for a period of approximately 1 hour to this suspension. The pH of the suspension when this addition is completed is 0.92; it is then increased to 4.8 by adding a 1M solution of sodium carbonate, and after approximately 60 minutes the pH is increased to 6 by means of a further addition of sodium carbonate. The suspension is then heated to a temperature of 90° C. and is maintained at this temperature for approximately 1 hour.

The solid is separated from the suspension by means of filtering and washing. It is then re-suspended in 2 liters of 0.1M solution of sodium carbonate. An argon flow is bubbled through the suspension, which is contained in a three-necked flask and is being gently agitated mechanically, until the air is entirely removed. The argon flow is then replaced by a hydrogen flow and the suspension is heated to a temperature of 80° C. The suspension is maintained at 80° C. for approximately 2 hours. The hydrogen flow is then replaced by an argon flow, and the suspension is cooled to 50° C. 500 $cm^3$ of aqueous solution of copper formate containing 4.5 g Cu is added slowly and continuously for a period of approximately 30 minutes to this suspension, and agitation of the suspension is continued for approximately 2 hours. The catalyst is filtered and washed until there are no chlorides left in the washing waters. The wet catalyst which has a ruthenium, palladium and copper base is kept moist in a sealed container, and has the following concentrations in weight of the activated metals: 2% Ru, 5% Pd and 1.5% Cu.

EXAMPLES 2–4 production of lower polyhydric alcohols.

The catalyst prepared according to example 1 is used for the conversion of sorbitol to lower polyhydric alcohols in various experimental conditions and using the following general method.

250 cm³ of aqueous solution containing 80 g sorbitol, 5.5 g calcium hydroxide and a variable amount of catalyst is introduced into an autoclave which has a volume of 500 cm³, and is provided with a manometer, a mechanical, magnetically driven agitator with four inclined blades, wash-plates, and a heating system. The autoclave is closed and the air it contains is eliminated by washing with inert gas. The inert gas is then replaced by hydrogen, and the autoclave is loaded under pressure to 13 MPa using hydrogen at ambient temperature. The heating and the agitation at 660 rpm are then begun. The required temperature is reached after approximately 1 hour, and is maintained for 2 hours. The pressure is increased to 15–19 MPa by the effect of heating, and then drops to 12–16.5 MPa owing to reaction. After the two-hour period the autoclave is cooled down by supplying water to the cooling jacket until ambient temperature is reached, and before the autoclave is de-pressurised a gas sample is collected for analysis. The reaction fluid is then discharged and is separated from the catalyst by filtration.

The gas sample collected is analysed by gas chromatography in order to ascertain the presence of any hydrocarbons (methane, ethane, ethylene etc) and carbon dioxide. The reaction fluid is analysed by means of high pressure liquid chromatography (HPLC).

The fluid product contains mainly 1,2-propylene glycol, ethanediol, glycerol, lactic acid and a smaller amount of butanediol and monovalent acids. The gas contains small amounts of methane and traces of carbon dioxide.

The results of examples 2–4 for three different molar ratios of sorbitol/ruthenium in the reactive medium are given in tables 1 and 2 hereinafter, relative respectively to the operative conditions and distribution of the reaction products.

TABLE 1

| Example | Temp. (°C.) | Molar ratio sorbitol/ruthenium | Conversion (% sorbitol) |
| --- | --- | --- | --- |
| 2 | 250 | 446 | 75 |
| 3 | 250 | 222 | 87.6 |
| 4 | 250 | 111 | 97.5 |

TABLE 2

| | | | Distribution of products (% of carbon atoms) | | | | | |
| --- | --- | --- | --- | --- | --- | --- | --- | --- |
| Example | methane | monovalent alcohols | ethanediol | 1-2 propylene glycol | butanediol | glycerol | lactic acid | others |
| 2 | 4.0 | 7.5 | 18.3 | 33.2 | 4.8 | 11.4 | 15.3 | 5.5 |
| 3 | 4.8 | 8.8 | 17.2 | 34.4 | 5 | 10.7 | 13.0 | 6.1 |
| 4 | 9.2 | 6.3 | 14.4 | 36.0 | 6.3 | 7.1 | 10.3 | 10.4 |

The results in tables 1 and 2 show that a decrease of the sorbitol/ruthenium ratio in the reactive medium lead to an increase in the conversion, however to the detriment of selectiveness as far as the gaseous products (methane) are concerned.

EXAMPLES 5–8

The catalyst obtained according to example 1 is used in the conversion of sorbitol according to the methods in examples 2 to 4, at various reaction temperatures. The results of these tests are given in tables 3 and 4 hereinafter.

TABLE 3

| Example | Temp. (°C.) | Molar ratio sorbitol/ruthenium | Conversion (% sorbitol) |
| --- | --- | --- | --- |
| 5 | 275 | 222 | 96.3 |
| 6 | 250 | 222 | 87.6 |
| 7 | 225 | 222 | 75.4 |
| 8 | 200 | 222 | 79.4 |

TABLE 4

| | | | Distribution of products (% of carbon atoms) | | | | | |
| --- | --- | --- | --- | --- | --- | --- | --- | --- |
| Example | methane | monovalent alcohols | ethanediol | 1-2 propylene glycol | butanediol | glycerol | lactic acid | others |
| 5 | 10.4 | 9.7 | 15.4 | 30.6 | 3.7 | 4.4 | 11 | 14.8 |
| 6 | 4.8 | 8.8 | 17.2 | 34.4 | 5.0 | 10.7 | 13 | 6.1 |
| 7 | 3.2 | 7.0 | 17.5 | 35.4 | 4.4 | 13.5 | 14.4 | 4.6 |
| 8 | 0.2 | 3.0 | 17.4 | 40.5 | 5.4 | 11.6 | 10.6 | 11.3 |

EXAMPLES 9–11

The catalyst prepared according to example 1 is used for the conversion of sorbitol at various reaction temperatures, according to the method in examples 2–4. The operative conditions and results of the tests are given in tables 5 and 6 hereinafter.

TABLE 5

| Example | Temp. (°C.) | Molar ratio sorbitol/ruthenium | Conversion (% sorbitol) |
| --- | --- | --- | --- |
| 9 | 250 | 111 | 97.5 |
| 10 | 225 | 111 | 87.5 |
| 11 | 200 | 111 | 80.0 |

TABLE 6

| | Distribution of products (% of carbon atoms) | | | | | | |
|---|---|---|---|---|---|---|---|
| Example | methane | monovalent alcohols | ethanediol | 1-2 propylene glycol | butanediol | glycerol | lactic acid | others |
| 9 | 9.2 | 6.3 | 14.4 | 36.0 | 6.3 | 7.1 | 10.3 | 10.4 |
| 10 | 5.1 | 1.7 | 15.8 | 34.1 | 4.1 | 14.6 | 10.9 | 13.7 |
| 11 | 2.34 | 6.8 | 15.5 | 33.3 | 3.6 | 15.4 | 12.2 | 10.9 |

EXAMPLES 12–14

The catalyst (100 cm$^3$) prepared according to example 1 is loaded in a tubular fixed bed reactor which has a descending and equally distributed flow, provided with a gas—fluid separator at the reactor outlet, a reaction fluid supply tank and a hydrogen gas tank. The reactor has a diameter of 20.5 mm (the height of the catalytic bed is 30 cm) and is equipped with a coaxial thermocouple which has 3 temperature measurement areas, disposed at 2.5, 15 and 28 cm below the topmost level of the catalytic bed. Above the catalytic bed there is a layer of inert material 7.5 cm deep, which ensures that the reagents are satisfactorily mixed before coming into contact with the catalytic bed itself.

The reactor is closed and is connected to a system for supply of the reagents and discharge of the products. The system is pressurised with nitrogen in order to check its airtightness. The reactor is then supplied at the test pressure with 2 flows: a mixed hydrogen—water flow obtained by injecting water into the hydrogen current, and a second flow of deionised water at ambient temperature. Before the two flows reach the catalytic bed they are thoroughly mixed through the layer of inert material. The reactor is then heated until it reaches the test temperature in approximately 2 hours. In these conditions the water flow is replaced by a flow of aqueous sorbitol solution containing sodium hydroxide. After approximately 8 hours the temperature and spatial velocity (LHSV) are in a steady state. After this stabilisation period collection of the chemical reaction products at two-hourly intervals begins. The fluid samples of the reaction products are analysed by means of high pressure liquid chromatography (HPLC). The gas output from the gas—fluid separator is measured and analysed by means of gas chromatography in order to ascertain the presence of any hydrocarbons (methane, ethane etc) and carbon dioxide. The fluid product contains mainly 1.2-propylene glycol, ethanediol, butanediol and a smaller amount of glycerol, lactic acid and monovalent alcohols, as well as products such as erythritol and pentanediol. The gas output from the reactor contains hydrogen and traces of carbon dioxide. The results of examples 12–14 for two different reaction temperatures and two different LHSV values are contained in tables 7 and 8 hereinafter, relative respectively to the operative conditions and distribution of the reaction products.

TABLE 7

| Example | Total pressure (MPa) | Temp. (°C.) | S = supply (ppm) | Sorbitol/NaOH (molar ratio) | H$^2$/Sorb. (molar ratio) | LHSV (h$^{-1}$) | Conversion (% sorbitol) |
|---|---|---|---|---|---|---|---|
| 12 | 15 | 250 | 0 | 3 | 9 | 1 | 97 |
| 13 | 15 | 225 | 0 | 3 | 9 | 1 | 96 |
| 14 | 15 | 225 | 0 | 3 | 9 | 0.667 | 99.4 |

TABLE 8

| Example | methane | monovalent alcohols | ethanediol | 1-2 propylene glycol | butanediol | glycerol | lactic acid | others |
|---|---|---|---|---|---|---|---|---|
| 12 | 2 | 5.6 | 18 | 43 | 15 | 5.8 | 4.4 | 6.2 |
| 13 | 0.4 | 2.8 | 18.5 | 48 | 12.8 | 7.5 | 3.3 | 6.7 |
| 14 | 0.2 | 2.6 | 18.3 | 47.3 | 13.3 | 5.6 | 3.6 | 9.1 |

We claim:

1. A method for preparing a catalyst for hydrogenolysis reactions of higher polyhydric alcohols, said method comprising the steps of:

(a) preparing an aqueous solution comprising a compound of ruthenium and a second metal compound selected from the group consisting of palladium, platinum and rhodium compounds;

(b) contacting the aqueous solution with an aqueous suspension of an activated carbon, and regulating the pH by adding an alkaline agent until a value of between 4.5 and 8 is obtained;

(c) heating to a temperature of 60° to 100° C. for a time sufficient to cause the formation of a solid comprising compounds of the metals deposited on the activated carbon;

(d) separating the solid;

(e) suspending the solid obtained from the separation in an alkaline solution and hydrogenating the suspension thus obtained with gaseous hydrogen at a temperature of between 60° and 100° C. for a time sufficient to give rise to an intermediate catalyst comprising the metals in their metallic state deposited on the activated carbon;

(f) adding to the suspension an aqueous solution comprising copper at a temperature lower than 50° C. and maintaining the suspension at this temperature, under agitation, for a time sufficient to give rise to depositing of the copper on the intermediate catalyst, thereby forming the catalyst; and (g) recovering the catalyst, the concentration of the metals in the aqueous solution of step (a) and the copper solution of step (f) being such that the catalyst comprises:
  (i) 0.5 to 5 weight % ruthenium;
  (ii) 1 to 10 weight % of a metal selected from the group consisting of palladium, platinum and rhodium; and
  (iii) 0.5 to 2.5 weight % copper, the weight % of copper being lower than the weight % of the metal in (ii).

2. The method of claim 1, in which the activated carbon is in granulated form and has the following characteristics:
  (a) a specific surface area of 600 to 1000 m$^2$/g;
  (b) a total pore volume of 0.5 to 1.2 cm$^3$/g;
  (c) an apparent specific weight (bulk density) of 0.45 to 0.55 g/cm$^3$;
  (d) an actual specific weight of 1.9 to 2.3 g/cm$^3$;
  (e) a total volume of micropores having a radius smaller than 75 Å of 0.4 to 0.55 cm$^3$/g; and
  (f) an ash content of 3 to 5 weight %.

3. The method of claim 2 in which the aqueous solution in step (a) is prepared by dissolving in water ruthenium trichloride and a palladium compound selected from the group consisting of H$_2$PdCl$_4$ and Na$_2$PdCl$_4$.

4. The method of claim 2, in which the copper solution of step (f) is prepared by dissolving copper formate in water.

* * * * *